United States Patent [19]

Petersen

[11] Patent Number: 5,554,168
[45] Date of Patent: Sep. 10, 1996

[54] DEVICE FOR CLOSING THE OPERATION WOUND AFTER PUNCTURE OF ARTERIA FEMORALIS OR VENA FEMORALIS

[75] Inventor: Anne L. Petersen, Greve, Denmark

[73] Assignee: LL Medico APS, Denmark

[21] Appl. No.: 157,040

[22] PCT Filed: May 29, 1992

[86] PCT No.: PCT/DK92/00171

§ 371 Date: Jan. 13, 1994

§ 102(e) Date: Jan. 13, 1994

[87] PCT Pub. No.: WO92/21297

PCT Pub. Date: Dec. 10, 1992

[30] Foreign Application Priority Data

Jun. 3, 1991 [DK] Denmark .................. 1055/91

[51] Int. Cl.$^6$ .................................. A61B 17/12
[52] U.S. Cl. .......................... 606/201; 128/691
[58] Field of Search .................. 606/201–204; 128/691

[56] References Cited

U.S. PATENT DOCUMENTS

| | | |
|---|---|---|
| 1,281,653 | 10/1918 | Plummer . |
| 2,455,068 | 11/1948 | Landry . |
| 3,625,219 | 12/1971 | Abrams et al. .................. 606/303 |
| 3,669,118 | 6/1972 | Colon-Morales . |
| 3,779,249 | 12/1973 | Semler .................. 606/201 |
| 4,233,980 | 11/1980 | McRae et al. . |
| 4,509,528 | 4/1985 | Sahota .................. 128/691 |
| 4,572,182 | 2/1986 | Royse . |
| 4,742,825 | 5/1988 | Freund et al. . |

FOREIGN PATENT DOCUMENTS

| | | |
|---|---|---|
| 0082009 | 6/1983 | European Pat. Off. . |
| 0295775 | 12/1988 | European Pat. Off. . |
| 219012 | 7/1909 | Germany . |
| 295027 | 12/1971 | Germany . |
| 149242 | 11/1931 | Switzerland . |

*Primary Examiner*—Gary Jackson
*Assistant Examiner*—William Lewis
*Attorney, Agent, or Firm*—Leonard Bloom

[57] ABSTRACT

The arrangement comprises a head which is mounted displaceably in the vertical direction on a swing arm on an upright member which can be fastened to the bottom frame of a hospital bed. The head is equipped with two pressure rods to whose lower end a pressure shoe is attached with a limited amount of swing and covered on the underside with a skid-proof material. The pressure rods can be moved from a starting position to a working position in which the pressure shoes rest against a compress in which position the pressure shoes exert equally large pressures in the vertical direction and in the horizontal direction of one pressure shoe towards the other. The arrangement can replace the manual work of closing an operation wound after a stab insertion into arteria femoralis or vena femoralis, and it is consequently labor-saving.

7 Claims, 3 Drawing Sheets

DEVICE FOR CLOSING THE OPERATION WOUND AFTER PUNCTURE OF ARTERIA FEMORALIS OR VENA FEMORALIS

The present invention relates to an arrangement for closing an operation wound after a puncture insertion into arteria femoralis or vena femoralis.

BACKGROUND ART

Numerous medical operations for the purpose of diagnosis and treatment are undertaken via the patient's blood vessels. These operations are performed in connection with diseases in the vessel system, such as arteriosclerosis or malformation or diseases in organs such as the brain, heart or kidneys.

The examinations are often undertaken via the artery in the groin, arteria femoralis, into which is inserted a probe or catheter. This procedure provides the physician with an option of examination, or probably post-treatment, of a patient without too many complications.

When the examination is over, the probe or catheter is withdrawn from the vessel leaving a bleeding wound. This wound is closed by the physician or a trained nurse pressing the vessel together (called compressing) for at least 20 minutes. In certain cases, it is necessary to compress for several hours for the wound in the vessel to close. Then the patient must lie with a sand bag on the place of the insertion for at least two hours or with a bandage of the kind which is the object of European Patent Application No. 0 295 775.

A medium-sized hospital carries out more than a thousand of these operations annually. The work of closing a wound after these operations is time-consuming and therefore takes up a large number of doctor's hours on an annual basis.

The following patents are pertinent to this problem:

From U.S. Pat. No. 3 669 118 an apparatus is known for displacement of a uterus.

From German patent No. 219012, Swiss patent No. 149242, U.S. Pat. No. 1,281,653 and European patent application No. 0 082 009 are known various devices designed to exert a pressure on an artery in such a way that the transport of blood through the artery is hampered or stopped.

From U.S. Pat. No. 2,455,068 an apparatus is known which can be inserted into the throat of a patient whose tonsils have been taken out.

From Austrian patent No. 295027 and U.S. Pat. Nos. 3,625,219, 3,779,249, 4,233,980, 4,572,182 and 4,742,825 apparatuses are known which can be used to exert pressure on the actual place of puncture insertion after the catheter is removed. These apparatuses have the drawback that they either only exert a pressure in the vertical direction, or a pressure in the vertical direction in combination with horizontal pressures, with no resulting pressure in a defined direction. Furthermore, they are embodied in such a way that—when arranged in position—they prevent inspection of the place of insertion. These known apparatuses have not proved well-suited in practice, and therefore manual compression is used.

It is the purpose of the present invention to describe an arrangement which is without the drawbacks of the known apparatuses, and which when in use, can greatly reduce the work of closing a wound after a puncture insertion of the described nature.

SUMMARY OF THE INVENTION

By use of the present invention, it is possible, among other things, for the place of puncture insertion to be inspected, and that the device therefore, can be placed in the correct position.

It has been demonstrated in scientific examinations that the device according to the invention can be used on 94% of all patients and that there is an average time saving of 15 minutes per patient.

The invention will be explained in detail below with reference to the drawings.

DESCRIPTION OF THE PREFERRED EMBODIMENTS

Figure 1:
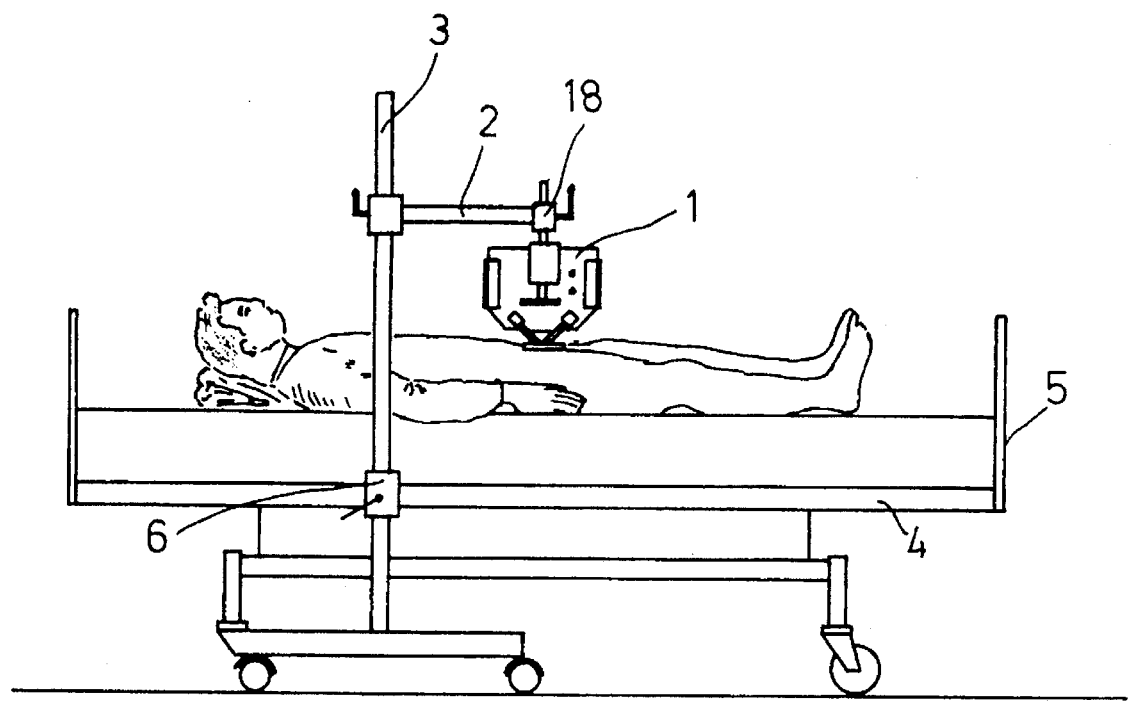
FIG. 1 is a schematic presentation of an arrangement according to the invention mounted on a hospital bed.
Figure 2:
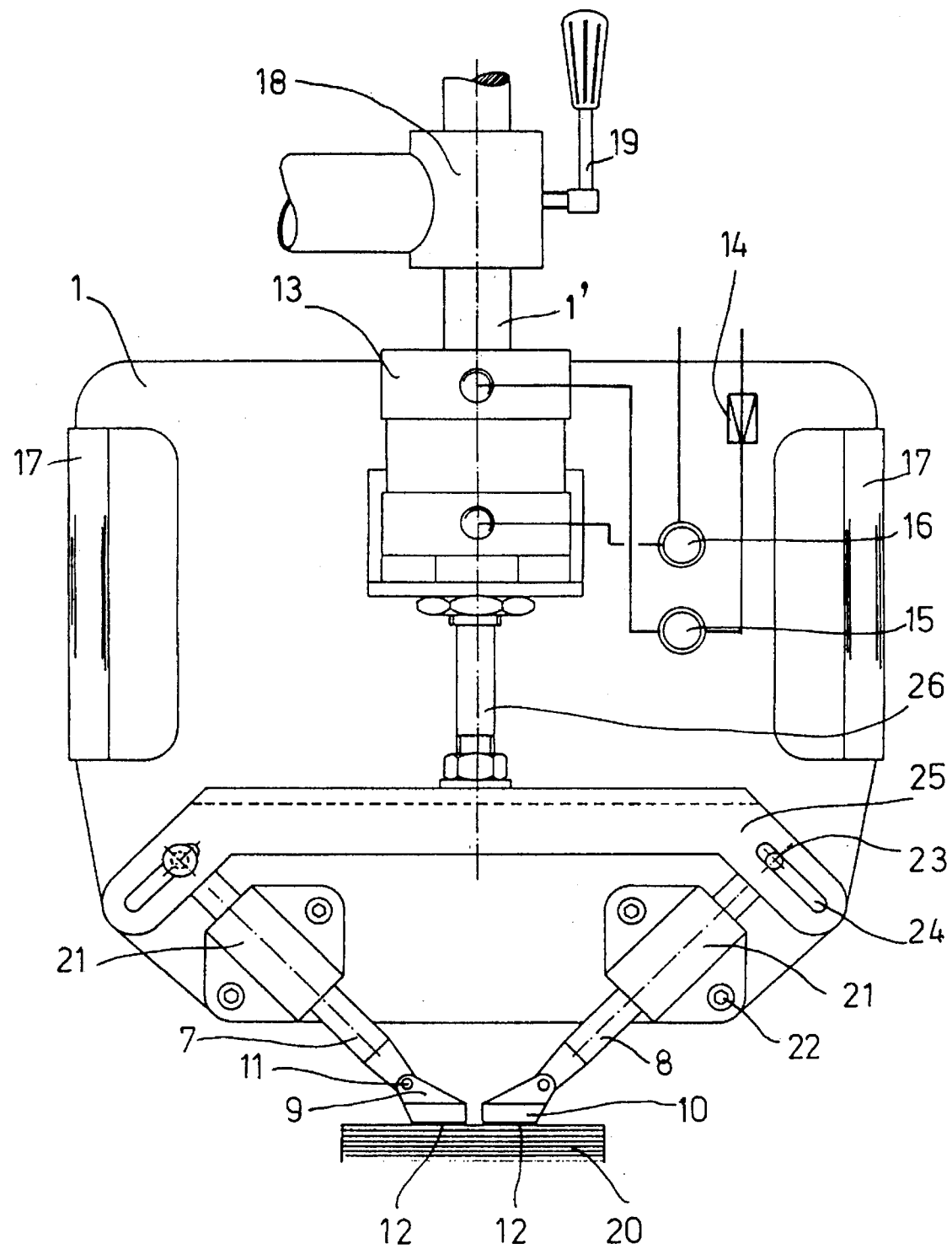
FIG. 2 shows, in a larger scale, a preferred embodiment of a head for the device according to the invention with certain components left out.
Figure 3:
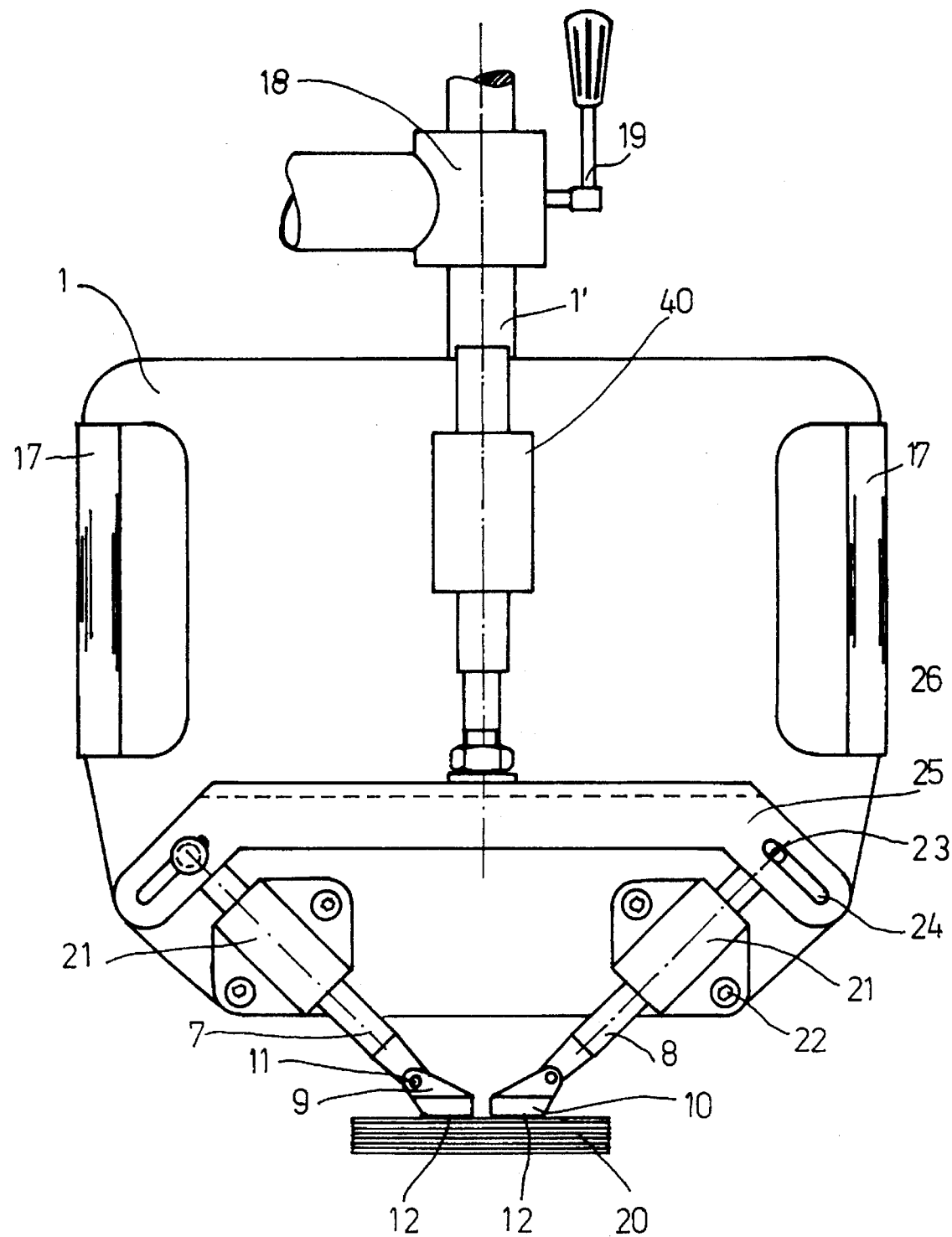
FIG. 3 shows a preferred embodiment with a push/pull mechanism driven by an electric motor.

As shown in FIG. 2, the pressure device is embodied with a connector rod 1', which is movable in the vertical direction in relation to the arm 2 and a pressure shoe, which can be moved in the vertical direction in relation to the connector rod 1' so that the pressure device can be moved from an initial position to a working position in which the pressure shoe comes into contact with, and exerts a vertical pressure on, the artery. A head 1 for an arrangement according to the invention is embodied with two pressure rods 7, 8.

At the lower end of each pressure rod 7, 8 a pressure shoe 9 and 10 respectively, is attached by means of pins 11. Each pressure shoe 9, 10, has a limited amount of swing movement.

The underside of each pressure shoe has a coating 12 which is skid-proof and elastic.

The pressure rods 7, 8 can be raised to a starting position and lowered to a working position, for example by means of a compresses air cylinder 13.

The compressed air cylinder 13 can be single-acting and loaded with a spring pressure in the downward or upward direction, or it can be double-acting. The pressure exerted by the compressed air cylinder can be regulated, for example by means of an adjustable reduction valve 14, which can be equipped with a pressure indicator showing the set pressure.

The compressed air cylinder can be activated in the downward and upward directions through push buttons 15 and 16, respectively.

The head 1 can be embodied with two handles 17 and firmly held in a swing arm 2 with a clamping mount 18 with a tightening screw 19. The head 1 may also be raised and lowered in relation to the swing arm 2 by means of a separate, not shown, drive cylinder in which latter case the pressure rods 7, 8 can be activated by an arrangement of weights and/or springs.

In the working position, each pressure shoe 9, 10 rests against a compress 20, which covers the wound to be healed. The pressure rods 7, 8 exert a vertical, downward directed pressure, each through its own shoe 9 and 10, respectively, on the compress 20. This pressure is of the same force in both rods. In addition, a horizontal pressure is exerted from the pressure rods on each pressure shoe 9, 10 in the direction of one pressure shoe towards the other. These horizontal pressures are of the same force in the two pressure rods and of the order of 12.5–15 kp.

As shown in FIG. 2 the two pressure rods 7 and 8 can be arranged so that they converge in the downward direction and form equally wide angles, e.g. 45°, to the horizontal. The pressure rods can be displaceably mounted each in its own sliding shoe 21. The sliding shoes can be adjustably mounted on the head 1, for example by means of screws 22. The sliding shoes can be adjusted so that the mutual distance between the pressure shoes 9 and 10 in the working position is 0.2–2.0 mm.

At its upper end, each pressure rod 7, 8 is embodied with a stud or bearing 23 which can move in a track 24 in a traverse 25 fastened to the piston rod 26 of the drive cylinder 13.

Instead of a compressed air cylinder, it is also possible to use a push/pull mechanism driven by an electric motor 40, which can be coupled to an end stop, e.g. a microswitch. Between this mechanism and the traverse 25, it is possible also to install a friction clutch. Furthermore, the upright 3 can be detached and dimensioned so that a certain vertical overload will tilt it.

The invention claimed is:

1. A device adapted for closing an operation wound after insertion of a catheter in an artery, the device comprising:

an upright member with a horizontal arm, a connector rod connected to the horizontal arm, a head adjustably and swingably mounted on a vertical axis on the connector rod, the head being vertically movable from an initial position to a working position, a first and a second pressure rod, each carried by the head distal from the horizontal arm, the first and the second pressure rods each having a lower end, two pressure shoes, a respective shoe mounted with a limited amount of swing on the respective lower ends of the first and the second pressure rods, each pressure shoe having an underside, each underside having a skidproof coating thereon, wherein when the head is moved to the working position, each pressure shoe contacts a respective compress, the pressure shoes being able to exert a uniform yielding and constant vertical pressure on the wound and further being able to exert a horizontal pressure against the wound from one pressure shoe to the other, and wherein the head is so oriented that the horizontal pressure is in a longitudinal direction with respect to the artery.

2. The device according to claim 1, wherein an elevating means is provided proximal to the horizontal arm so that the head can be raised and lowered.

3. The device according to claim 1, further comprising a drive means connected to the pressure rods wherein the pressure rods can be raised or lowered in the head.

4. The device of claim 3, wherein the drive means is an electric motor.

5. The device of claim 3, further comprising each pressure rod having an upper end, the upper end of each pressure rod being connected to a respective bearing, each bearing moving in a respective track in a traverse, the traverse being connected to a piston rod of a drive cylinder such that the traverse is moved in an oblique direction.

6. The device according to claim 1 wherein means for the registration and regulation of the pressure rods (7,8) in their working position comprise an adjustable valve to control pressure applied to the respective rods and a pressure indicator to show the pressure.

7. The device according to claim 1, further comprising a first and a second sliding shoe adjustably mounted on the head in an inclined downward direction such that the sliding shoes oppose one another, the first pressure rod being slidably mounted in the first sliding shoe and the second pressure rod being slidably mounted in the second sliding shoe.

\* \* \* \* \*